United States Patent [19]
Della Valle

[11] 4,296,039
[45] Oct. 20, 1981

[54] SELECTED PROCESS FOR PRODUCING MONOHALOGENATED DERIVATIVES OF 7-HYDROXY-COUMARIN

[75] Inventor: Francesco Della Valle, Padua, Italy

[73] Assignee: Fidia S.p.A., Padua, Italy

[21] Appl. No.: 112,223

[22] Filed: Jan. 15, 1980

Related U.S. Application Data

[62] Division of Ser. No. 952,460, Oct. 18, 1978, abandoned.

[30] Foreign Application Priority Data

Nov. 17, 1977 [IT] Italy ............................. 29765 A/77

[51] Int. Cl.³ ................. C07D 311/08; C07D 413/06; C07D 405/06
[52] U.S. Cl. ............................... 260/343.45; 544/151; 546/196
[58] Field of Search .................. 260/343.45; 544/151; 546/196

[56] References Cited

U.S. PATENT DOCUMENTS

| 3,259,635 | 7/1966 | Ritter et al. | 260/343.45 |
| 3,515,721 | 6/1970 | Ritter et al. | 260/343.45 |
| 3,923,836 | 12/1975 | Bender et al. | 260/343.44 |

FOREIGN PATENT DOCUMENTS 1146792  3/1969  United Kingdom ........... 260/343.44

Primary Examiner—Henry R. Jiles
Assistant Examiner—Jane T. Fan
Attorney, Agent, or Firm—Birch, Stewart, Kolasch and Birch

[57] ABSTRACT

A selective process is described for producing monohalogenated derivatives of 7-hydroxy coumarin wherein the halo substituent is at the desired position and the final product is free of other monohalogenated isomers. The resulting products, especially those wherein the halo substituent is at the 8 position, have valuable specific coronary vasodilating activity.

5 Claims, No Drawings

SELECTED PROCESS FOR PRODUCING MONOHALOGENATED DERIVATIVES OF 7-HYDROXY-COUMARIN

This is a division of application Ser. No. 952,460 filed Oct. 18, 1978 now abandoned.

BACKGROUND OF THE INVENTION

1. Field of the Invention

The present invention relates to a selective process for the preparation of basic coumarin derivatives (I) and of their salts formed by the reaction with organic and inorganic salts. In the formula I

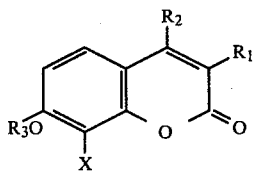

$R_1$ is selected from alkyl groups having thereon basic substituents, such as piperidino ethyl, morpholino ethyl, diethylamino ethyl or diethylamino propyl; $R_2$ is selected from the group consisting of hydrogen, alkyl and aryl; $R_3$ is selected from the group of alkyl radicals substituted with a basic group, an alkenyl group, a carboxy alkyl group or an alkoxy carbonyl alkyl group; and wherein X represents a halogen atom in the 8 position.

The process according to the invention makes it possible to obtain as final products monohalogenated derivatives of 7-hydroxycoumarin of the formula:

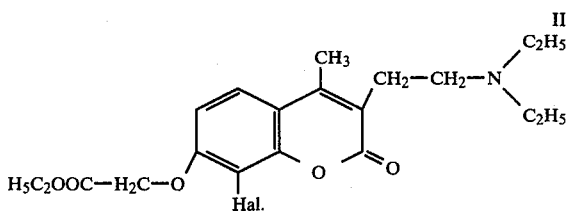

which, by virtue of the selective process which forms the object of the present invention, give the certainty that the halogen atoms are in position 8; said final products, as it will be shown hereafter, are thus obtained in grade and purity sufficient to exercise a vasodilatory action effectively, in particular with respect to coronary vessels in animals and humans.

2. Prior Art

It is already known a pharmaceutical product under the generic name of 'carbochromene' of the general formula:

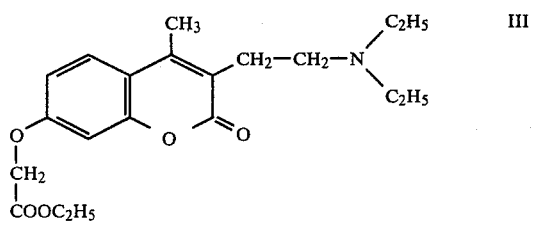

There are also patented (see U.S. Pat. No. 3,515,721) some mono- and di-halogen derivatives obtained according to the scheme described in the cited patent and having the general formula:

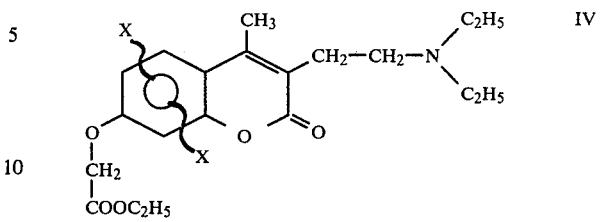

Said compounds also possess specific coronary vasodilatory activity but to a lower degree (see compound No. 4 and 10 in the attached table), according to data furnished in the said patent, with respect to carbochromene (compound No. 2 of the table).

Furthermore, in said patent, it is stated that there is obtained in the case of monohalogenated derivatives a single final product and only in the corresponding British specification No. 1,146,792 it is specified that the halogen is in position 8.

Such product is in fact composed of a mixture of derivatives of 7-hydroxy-coumarin and there are also present therein compounds having a halogen atom in the position indicated by X: position 8 or position 6.

The uncertainty on where the halogen is located is due to the procedure followed by the patent; since the halogen is introduced during an intermediate phase of the process, it is not possible to determine with certainty what position will the halogen occupy.

DESCRIPTION OF THE INVENTION

Surprisingly, according to the present invention studies on the activity of mono-halogenated derivatives having the halogen atom in position 8, have revealed that such monohalogenated derivatives possess a vasodilatory activity in animals notably superior to that of carbochromene (compare compound No. 3 with compounds Nos. 6 and 9 in Table I) and a melting point different from those indicated in said prior patents as noted in Table I.

According to the present invention, the process of preparing the compounds of the invention comprises (a) reacting a 2-halo-resorcinol of the formula:

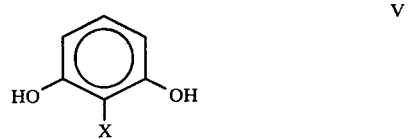

with a β-keto ester to obtain an intermediate of the formula:

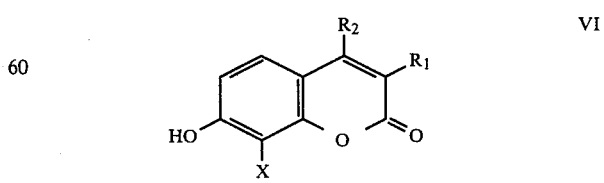

wherein $R_1$, $R_2$ and X are as indicated in formula I hereinabove; and (b) further reacting said intermediate VI with a compound of the formula $R_3$-hal, wherein $R_3$ is as indicated in formula I, and hal indicates a halogen atom such as Br-, Cl- or I- for example, in the presence of an acid-binding agent to obtain the desired compound.

Another process also according to the present invention comprises reacting a mon-alkylated 2-halo-resorcinol of the formula:

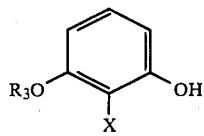
VII wherein $R_3$ and X are as indicated above, with β-keto ester to obtain the desired product.

The following examples are given for the purpose of illustrating the present invention. All temperatures are in degrees centigrade.

EXAMPLE 1

8-chloro-3-(β-diethylaminoethyl)-4-methyl-7-hydroxy-coumarin

To 50.6 g of 2-chloro-resorcinol (prepared according to N. Schamp, Bull, Soc. Chim. Belg., 73, 35 (1946): Hans Verner Wanzlick and Steffi Mohrmann, Chem. Ber., 96, 2257 1963) there are added 80.2 g of the ethyl ester of α-(β-diethyl aminoethyl) acetacetic acid and 66.5 g of p-toluene-sulfonic acid.

The mixture is slowly poured into 770 g of polyphosphoric acid while stirring; the temperature of the mixture should not exceed 35°.

After about 24 hours there is added 1 kg of ice. There is obtained as a precipitate the salt of 8-chloro-3(β-diethylaminoethyl)-4-methyl-7-hydroxy-coumarin which is separated by filtration.

The 8-chloro-3-(β-diethylaminoethyl)-4-methyl-7-hydroxy-coumarin is freed with an aqueous solution of sodium carbonate. Yield 70%, m.p. 220°.

The hydrochloride of the 8-chloro-3-(β-diethylaminoethyl)-4-methyl-7-hydroxy-coumarin produced by the process melts at 246°-266°. The prior art (R. Beyerle and R. E. Nitz, British specification No. 1,146,792 page 4, lines 123-127) gives a melting point for the hydrochloride at 278°. The solid obtained by the cited authors (by chlorination of the 3(β-diethylaminoethyl)-4-methyl-7-hydroxy-coumarin) does not correspond to the hydrochloride of 8-chloro-3(β-diethylaminoethyl)-4-methyl-7-hydroxy-coumarin, but to a mixture containing various compounds, among which the 6-chloro isomer.

In fact, the 6-chloro-3(β-diethylaminoethyl)-4-methyl-7-hydroxy-coumarin hydrochloride prepared according to the process of the invention, but starting with 4-chloro-resor cinol melts at 284°-287°.

There was then repeated the preparation described by R. Beyerle and R. E. Nitz.

A simple thin layer of chromatographic analysis showed that it consisted of a mixture of 6-chloro-3(β-diethylaminoethyl)-4-methyl-7-hydroxy-coumarin hydrochloride, of 8-chloro-3(β-diethylaminoethyl)-4-methyl-7-hydroxy-coumarin hydrochloride and of other compounds. [see table I (note)]

EXAMPLE 2

8-chloro-3(β-diethylaminoethyl)-4-methyl-7-ethoxycarbonylmethoxy-coumarin 50 g of 8-monochloro-3(β-diethylaminoethyl)-4-methyl-7-hydroxy-coumarin are suspended in 600 ml of acetone; there are then added 70 g of potassium carbonate and 65 g of ethyl monochloroacetate and the mixture is refluxed for 14 hours.

After filtration, the solution is evaporated under reduced pressure and the residue is dissolved in dilute acetic acid (15 ml acetic acid in 400 ml water).

The aqueous solution is made basic with ammonia; there is obtained a solid which after recrystallization from ethyl acetate gives the 8-chloro-3(β-diethylaminoethyl)-4-methyl-7-ethoxycarbonyl-methoxy-coumarin, m.p. 147°-8°. The hydrochloride melts at 219°-20°. The literature already cited in the first example gives, for the hydrochloride, a melting point of 188°. As it was indicated before, the solid obtained in the prior art corresponds to a mixture of compounds. [See table I (note)]

EXAMPLE 3

8-bromo-3-(β-diethylaminoethyl)-4-methyl-7-hydroxy-coumarin

To 14.2 g of 2-bromoresorcinol (prepared according to N. Schamp and H. DePooter, Bull. Soc. Chim. Belg., 75, 391, 1966) there are added 17.1 g of the ethyl ester of α(β-diethylaminoethyl) acetoacetic acid and 14 g of p-toluenesulfonic acid.

The mixture is slowly poured, with stirring, into 170 g of polyphosphoric acid; the temperature of the mixture should not exceed 35°.

After 24 hours there are added 300 g of ice. The salt of 8-bromo-3(β-diethylaminoethyl)-4-methyl-7-hydroxy-coumarin in which precipitates is collected by filtration.

The 8-bromo-3(β-diethylaminoethyl)-4-methyl-7-hydroxy-coumarin is freed with an aqueous solution of sodium carbonate. Yield 80%, m.p. 250°.

The bromohydrate of 8-bromo-3(β-diethylaminoethyl)-4-methyl-7-hydroxy-coumarin melts at 325°.

British patent No. 1,146,792 to Beyerle and Nitz as well as other patents, give a melting point of 261° for the bromohydrate. The solid obtained by the prior art by bromination of 3(β-diethylaminoethyl)-4-methyl-7-hydroxy-coumarin is composed by a mixture of compounds.

EXAMPLE 4

8-bromo-3(β-diethylaminoethyl)-4-methyl-7-ethoxycarbonylmethoxy-coumarin 20 g of 8-bromo-3(β-diethylaminoethyl)-4-methyl-7-hydroxy coumarin are suspended in 300 ml of acetone. There are then added 35 g of potassium carbonate and 25 g of ethyl monochloro-acetate and the mixture is refluxed for 20 hours.

After filtration, the acetone filtrate is evaporated under reduced pressure and the residue is dissolved in dilute acetic acid. The aqueous solution is made basic with ammonia. There is thus obtained the solid which, when recrystallized from ethyl acetate, gives the product, 8-bromo-3(β-diethylaminoethyl)-4-methyl-7-ethoxycarbonyl-methoxy-coumarin, m.p. 150°-151°. The hydrochloride of this product melts at 200°-201°. The prior art cited in Example 1 gives a melting point of 177° for this hydrochloride.

Following the previous reasoning, the solid obtained by the prior art consisted of a mixture of compounds.

EXAMPLE 5

Mono-ethoxycarbonyl methyl-2-chloro-resorcinol 31. g of 2-chlororesorcinol are treated with 800 ml of acetone. There are added 29 g of potassium carbonate and 26 g of ethyl chloracetate. The suspension is then refluxed for 48 hours.

After filtration, the acetone filtrate is evaporated. The residue gives 29 g of mono-ethoxycarbonyl methyl-2-chloro-resorcinol m.p. 75°–76°.

EXAMPLE 6

8-chloro-3($\beta$-diethylaminoethyl)-4-methyl-7-ethoxycarbonyl methoxy coumarin (starting with monoethoxycarbonyl methyl 2-chloro-resorcinol)

To 15 g of monoethoxycarbonyl methyl 2-chlororesorcinol there are added 15 g of the ethyl ester of $\alpha(\beta$-diethylaminoethyl) acetoacetic acid and 12 g of p-toluenesulfonic acid.

The mixture is poured slowly, with stirring, in 200 g of polyphosphoric acid; the temperature should not exceed 35°.

After 24 hours the mixture is treated as in Example 2. There is obtained a crystalline material, m.p. 147°–148°.

EXAMPLE 7

Evidence of Utility in Increasing Coronary Flux of Mammals: Experimental Conditions and Method for Measuring coronary Vasodilator Activity These studies were effected on dogs having a weight between 18 and 30 kg. The action of the compound was examined under anaesthesia immediately after surgery. The anaesthesia was induced with sodium thiopentone (15 mg/kg, e.v.) and maintained with chloralose (80–100 mg/kg, e.v.). Supplementary doses of chloralose were given during the experiment to keep the anaesthesia constant.

The animals were subjected to intermittent positive pressure ventilation. The preparation for surgery consisted in the installation of the following devices: electromagnetic flux transductor and a plastic probe (to mechanically zero the flux indicator in case of a temporary arrest of the blood flow) on the left circumflexed coronary artery which had been prepared through left toroacothomy; an electromagnetic flux transductor and a probe in the femoral artery; a catheter in the other femoral artery to record the arterial pressure; a catheter in the femoral vein adjoining the catheterized femoral artery, or in the external jugular vein, for the injection of the test materials; a catheter in the left ventricle through a common carotid to record the ventricular pressure and its first derivative (dp/dt); a catheter in the coronary sinuses (two dogs) for the withdrawal of venous blood in the left coronaries; a thin hypodermic needle (246) connected to a catheter in the left circumflexed coronary artery for the intracoronary injection of the test substances. The oxygen content in the coronary sinuses was measured with a Van Slyke apparatus.

The studies have been performed on the dogs 4–6 days after the installation of an electromagnetic flux transductor on the ascending aorta, a catheter in the ascending aorta to register the blood pressure and a catheter in the external jugular vein for endovenous injections.

This surgical preparation was performed under anaesthesia with sodium pentathol (30 mg/kg) under sterile conditions. During the experiment the animals are allowed to remain quiet on a padded bed, without sedatives and without restraining means; they were used to measure the cardiac output, left ventricular work per minute (cardiac throw for mean aortic pressure) length of the sistule (ejection phase) and the first derivative of the curve of aortic flux (df/dt) together with the blood pressure and cardiac frequency.

To measure the blood flow and blood pressure there were used respectively Biotronex No. 610 amplifiers and Battaglia Rangoni No. 1 1A transductors.

The data have been visually observed on a Hewlett Packard 4588 optical recorder. The vascular resistances for the coronary and femoral lumens have been calculated as the relationship between the mean arterial pressure in mm Hg and the blood flow in ml/min. The intracoronary and endovenous administration of the test substances was performed in a period of 20–30 seconds. The test substances were diluted in physiological solution (0.5 ml/kg).

The results obtained are set forth in the following Table I.

TABLE I:

| | Comparative Tests Showing Vasodilator Activity | | | | | |
|---|---|---|---|---|---|---|
| Substance | Dosage i.v. | Maximum Increase in Coronary Flux (Percent) | Length of action (minutes) | Change in Blood Pressure (Percent) | m.p. p.f. (°C.) | Pharmacological data from |
| (1) Papaverine | 0.8 | 23–24 | 8–10 | −20 | | U.S. Pat. No. 3,515,721 No. 3,259,635 |
| (2) 3($\beta$-diethylamino ethyl)-4-methyl-7-ethoxy carbonyl methoxy coumarin hydrochloride (carbochromene) | 2.8 | 67 | 75 | −4 | 159–160° C. | U.S. Pat. No. 3,259,635 |
| (3) Same as under (2) | 2.0 | 104 | 65 | −2 | 159–160° C. | our experimental data |
| (4) Product (1) described in example 3 of U.S. Pat. No. 3,515,721 | 2.0 | 38 | 40 | — | 188° C. | U.S. Pat. No. 3,515,721 |
| (5) Product (1) prepared by us following example No. 3 of U.S. Pat. No. 3,515,721 | 2.0 | 42 | 45 | — | 187–255° C. | our experimental |

TABLE I:-continued

| | Comparative Tests Showing Vasodilator Activity | | | | | |
|---|---|---|---|---|---|---|
| Substance | Dosage i.v. | Maximum Increase in Coronary Flux (Percent) | Length of action (minutes) | Change in Blood Pressure (Percent) | m.p. p.f. (°C.) | Pharmacological data from |
| (6) 8-monochloro-3(β diethylamino ethyl)-4-methyl-7-ethoxy carbonylmethoxy coumarin hydrochloride | 2.0 | 272 | 85 | ±0 | 219-220° C. | our experimental data - example 2 |
| (7) 6-monochloro-3(β diethylamino ethyl)-4-methyl-7-ethoxy carbonyl-methoxy coumarin hydrochloride | 2.0 | 70 | 50 | ±0 | 213° C. | our experimental data - |
| (8) 5-monochloro-3(β-diethylamino ethyl)-4-methyl-7-ethoxy carbonyl methoxy coumarin hydrochloride | 2.0 | 30 | 20 | ±0 | 150° C. | our experimental data - |
| (9) 8-monobromo-3(β-diethylamino ethyl)-4-methyl-7-ethoxy carbonyl methoxy coumarin hydrochloride | 2.0 | 210 | 70 | ±0 | 202-203° C. | our experimental data - example 4 |
| (10) -monobromo-3(β-diethylamino ethyl-4-methyl-7-ethoxy carbonyl methoxy coumarin hydrochloride | 2.0 | 37 | 30 | — | 177° C. | U.S. Pat. No. 3,515,721 |

(1) In reality it is the question of not a sole compound, but a mixture of compounds.
NOTE:
Example U.S. Pat. No. 3,515,721 3 has been repeated several times, the chloridation reaction (III paragraph, Example 3) was repeated several times. The results concerning the yield correspond to what is described in the patent. It is to be noted that the solid obtained results clearly to be a mixture formed by several compounds, among which it is possible to recognize 6-monochloro-3-β-diethyl-aminoethyl-4-methyl-7-hydroxy coumarin hydrochloride (chromatography on a thin layer using as eluent chloroform, methanol, ammonia 2N (containing 3% of ammonium acetate) 80:20:2). Quantitative determination allowed to ascertain in the final solid that in 8-monochloro-3-β diethylaminoethyl-4-methyl-7-hydroxy coumarin hydrochloride is present at the rate of 18% only. The alkylation reaction (I paragraph, Example 3) was repeated several times. The results concerning the yield correspond to what is described in the patent. It is to be noted that the solid obtained results clearly to be a mixture formed by several compounds among which it is possible recognize 6-monochloro-3-β-diethylaminoethyl-4-methyl-7-ethoxycarbonylmethoxy coumarin hydrochloride (chromatography on a thin layer using cycloexane-diethylamine-acetone 80:10:10). Quantitative determination allowed to ascertain in the final solid the 8-monochloro-3-β-diethylaminoethyl-4-methyl-7-ethoxycarbonylmethoxy coumarin hydro-chloride is present at the rate of 30% only.

What is claimed is:

1. Process for the preparation of pure 7-hydroxycoumarin derivatives of the formula I:

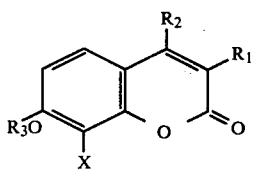

wherein X represents a halogen atom, $R_1$ is selected from the group consisting of piperidino ethyl, morpholino ethyl, diethylamino ethyl and diethylamino propyl, $R_2$ is selected from the group consisting of methyl and phenyl, and $R_3$ is selected from the group consisting of ethoxy-carbonyl-methyl and ethoxy-carbonyl-ethyl, which process comprises (a) reacting a 2-halo-resorcinol of the formula V:

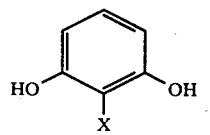

with a β-keto ester to obtain an intermediate of the formula

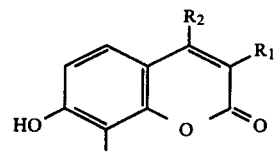

wherein $R_1$, $R_2$ and X are as hereinbefore indicated, and (b) subsequently reacting said intermediate VI with a compound of the formula $R_3$-Halogen, wherein $R_3$ is as before defined, in the presence of an acid-binding agent to obtain the desired compound I.

2. Process for the preparation of pure 7-hydroxycumarin derivatives of the formula I according to claim 1, which process comprises reacting a mono-alkyl 2-haloresorcinol of the formula VII:

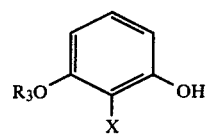

wherein $R_3$ is as defined in claim 1, with a β-keto ester.

3. A process as claimed in claim 1, wherein X is selected from the group consisting of chlorine and bromine.

4. A process as claimed in claim 1, wherein p-toluene sulfonic acid and/or polyphosphoric acid is used in step (a).

5. A process as claimed in claim 1, wherein an alkali metal carbonate is used as an acid binding agent.

* * * * *